United States Patent [19]

Zenker et al.

[11] Patent Number: 5,441,973
[45] Date of Patent: Aug. 15, 1995

[54] N-ACYL-4-PHENYL-PYRROLIDIN-2-ONES AND METHOD FOR PREPARING

[75] Inventors: Lothar Zenker, Radebeul; Helmut Wunderlich, Dresden; Dieter Lohmann, Radebeul; Angelika Rostock, Dresden; Christine Siegemund, Weinböhla, all of Germany; Artur V. Valdman, Moskau, U.S.S.R.; Tatjana A. Voronina, Moskau, U.S.S.R.; Ilmira C. Rachmankulova, Moskau, U.S.S.R.; Oleg M. Glozman, Moskau, U.S.S.R.; Taisija L. Garibova, Moskau, U.S.S.R.; Larisa M. Mescerjakova, Moskau, U.S.S.R.; Ljudmila A. Zmurenko, Moskau, U.S.S.R.; Sergej B. Seredenin, Moskau, U.S.S.R.; Grigorij G. Rozancev, Moskau, U.S.S.R.

[73] Assignee: Arzneimittelwerk Dresden G.m.b.H., Radebeul, Germany

[21] Appl. No.: 182,665

[22] Filed: Jan. 13, 1994

Related U.S. Application Data

[63] Continuation of Ser. No. 995,329, Dec. 23, 1992, abandoned, which is a continuation of Ser. No. 642,053, Jan. 16, 1991, abandoned.

[30] Foreign Application Priority Data

Jan. 31, 1990 [DE] Germany .......................... 3 37 440.6

[51] Int. Cl.$^6$ ................... A61K 31/455; A61K 31/40; C07D 401/02; C07D 403/02
[52] U.S. Cl. ..................... 514/343; 514/423; 514/340; 514/408; 546/268; 546/275; 546/281; 548/530; 548/539; 548/540
[58] Field of Search ................. 548/530; 546/281; 514/423, 343

[56] References Cited

U.S. PATENT DOCUMENTS

| | | | |
|---|---|---|---|
| 4,012,495 | 3/1977 | Schmiechen et al. | 548/540 |
| 5,227,395 | 7/1993 | Komatsu et al. | 514/408 |

FOREIGN PATENT DOCUMENTS

| | | |
|---|---|---|
| 0258983 | 8/1988 | German Dem. Rep. |
| 0048566 | 2/1990 | Japan |

*Primary Examiner*—Mary C. Lee
*Assistant Examiner*—Laura L. Stockton
*Attorney, Agent, or Firm*—Schweitzer Cornman & Gross

[57] ABSTRACT

The invention is directed to N-acetyl-4-phenyl-pyrrolidin-2-ones, which, because of their pronounced cerebroprotective effect in human medicine, can be used for the prophylaxis and treatment of cerebral functional disorders. Pursuant to the invention, these compounds are synthesized by reacting 4-phenyl-pyrrolidin-2-ones with a reactive derivative of a carboxylic acid, or by cyclizing N-acylaminobutyric acid derivatives.

4 Claims, No Drawings

N-ACYL-4-PHENYL-PYRROLIDIN-2-ONES AND METHOD FOR PREPARING

This is a continuing application of U.S. Ser. No. 07/995,329, filed on Dec. 23, 1992, which is a continuing application of U.S. Ser. No. 07/642,053, filed on Jan. 16, 1991, both now abandoned.

FIELD OF THE INVENTION

The present invention relates to novel N-acyl-4-phenyl-pyrrolidin-2-ones and a method for their preparation. These compounds have a pronounced cerebroprotective action and are well tolerated by the human organism. In human medicine, they can be used suitably for the prophylaxis and treatment of cerebral functional disorders.

BACKGROUND OF THE INVENTION

The synthesis of 4-(polyalkoxyphenyl)-pyrrolidin-2-ones is described in German Democratic Republic patent No. 119,229, as having a sedating, neuroleptic effect on the central nervous system.

4-(4-chlorophenyl)-pyrrolidin-2-one is mentioned in Japanese patent No. 7,016,692. It is not substituted at the nitrogen atom, and is said to have an anticonvulsive effect.

U.S. Pat. No. 4,443,616, describes the preparation of pyrrolidin-2-ones from 3-pyrrolidin-2-ones. The product is stated to have a CNS effect but this is not further explained in greater detail.

According to Japanese patent No. 3,246,328, aside from various CNS effects, N-acyllactams that are not substituted in the 4 position, also show antiamnestic effects in animal experiments. Our own experiments have shown that the cerebroprotective properties of these compounds are only weakly manifested especially when compared to the much more pronounced activity of the compounds of the present invention.

Moreover, N-dipropylacetyllactams with a 5-, 6- or 7-membered lactam ring are known e.g. from the German Democratic Republic patent No. 256 694. These lactams in animal experiment exhibit in addition to anticonvulsive effects, also antihypoxic and nootropic effects. On the other hand, the new compounds of the present invention show a decisive and, for the therapeutic application in man advantageous shift in the pharmacological spectrum, while having a decreased toxicity.

The compounds of the present invention show substantial advantages compared to known substances with nootropic activity, which were introduced some time ago in medical practice. For example, the antiamnestic effect of the compounds of the present invention is more than eight hundred times that of the standard nootropic drugs, piracetam and meclofexonate.

DESCRIPTION OF THE INVENTION

The novel compounds of the present invention are those of formula I

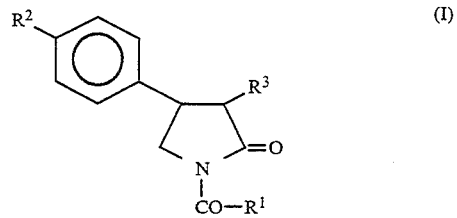

wherein $R^1$ is a linear or branched, saturated or unsaturated, $C_{1-9}$ alkyl, aryl, aralkyl, or heteroaryl residue which can be substituted by a halogen atom or alkoxy having a $C_{1-3}$ alkyl moiety, or a p-chlorophenoxymethyl residue, $R^2$ is hydrogen, halogen, or alkoxy with $C_{1-3}$ alkyl moiety, and $R^3$ is hydrogen or carbalkoxy with $C_{1-3}$ in the alkyl moiety, and pharmaceutically acceptable salts thereof.

Suitable compounds of formula I include:
N-dipropylacetyl-4-phenyl-pyrrolidin-2-one;
N-dipropylacetyl-4-(4-chlorophenyl-pyrrolidin)-2-one;
N-(4-methyoxybenzoyl)-4-phenyl-pyrrolidin-2-one;
N-(4-methyoxybenzoyl)-4-(4-chlorophenyl)-pyrrolidin-2-one;
N-(4-chlorophenyoxyacetyl)-4-phenyl-pyrrolidin-2-one;
N-(4-chlorophenoxyacetyl)-4-(4-chlorophenyl)pyrrolidin-2-one;
N-dipropylacetyl-3-carbethoxy-4-phenyl-pyrrolidin-2-one;
N-(4-chlorobenzoyl)-4-phenyl-pyrrolidin-2-one;
N-(4-methoxybenzoyl)-3-carbethoxy-4-phenyl-pyrrolidin-2-one;
N-nicotinoyl-4-phenyl-pyrrolidin-2-one; and
pharmaceutically acceptable salts thereof.

The compounds of formula I are normally oily or crystalline, generally colorless to slightly yellowish materials, which are not soluble in water.

Administration of a pharmaceutical preparation containing a therapeutically effective amount of one or more compounds of formula I manifests a cerebroprotective effect, and is effective for treating cerebral functional disorders.

The compounds of formula I can be prepared in accordance with the process of the present invention by reacting (i) a 4-phenyl-pyrrolidin-2-one of formula (II)

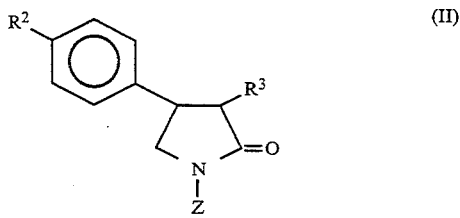

wherein

Z is hydrogen, or an alkali metal ion, and $R^2$ and $R^3$ have the same meaning as given above, or a pharmaceutically acceptable salt of formula II, with (ii) a reactive derivative of a carboxylic acid, which contains the hydrocarbon group $R^1$ as that substituent defined above.

Suitable $R^1$ moiety include, for example, methyl, ethyl, propyl, isopropyl, butyl, isobutyl, t-butyl, pentyl, 2-methylbutyl, 2,2-dimethylpropyl, hexyl, heptyl, 4-heptyl, octyl, nonyl, and 1,2-dimethylheptyl residues. The alkyl groups can also be unsaturated, such as vinyl, 1-propenyl, 2-propenyl, etc. As alkoxy groups, suitably methoxy, ethoxy and n- or isopropoxy groups can be employed.

The aryl group is suitably a phenyl moiety and the aralkyl group is suitably a cinnamoyl or tolyl group. Heterocyclic groups can include, for example, heterocyclic, nitrogen containing groups, such as the nicotinoyl group.

$R^1$ can also be substituted once or more than once, for example by halogen, suitably by fluorine, chlorine or bromine, or by hydroxy groups, such as 4-hydroxypropyl, or by amino groups, in which the nitrogen is optionally substituted by one or two suitably $C_{1-5}$ alkyl groups, or it can be a component of a 5- to 7-membered ring.

Particularly, the carboxylic acid anhydrides, most suitably the lower molecular weight, suitably $C_{2-4}$, carboxylic acids, and carboxylic acid halides, and carboxylic acid chlorides, which are easily accessible on an industrial scale, are suitably employed as reactive carboxylic acid derivatives.

Suitably the compound of formula II when Z is hydrogen, is reacted with activated carboxylic acid esters, such as pentachloro benzoates, to form the compounds of the present invention.

In a specific embodiment of the process of the present invention a salt of formula II, in which Z is an alkali metal moiety, is reacted with a carboxylic acid halide. Alkali salt, alkali metals, alkali amides or other reactive alkali derivatives, such alkali alcoholates or alkali hydroxides can be used to form the alkali salt.

It can be advantageous to use hydrogen halide acceptors, such as triethylamine, pyridine, N,N-dimethylaniline or alkali carbonates, to accelerate and complete the reaction of the compound of formula II with the carboxylic acid halide. The reaction of the compound of formula II with the reactive carboxylic acid derivative can be carried out in the presence, as well as in the absence of inert organic solvents. For example, aliphatic or aromatic hydrocarbons such as benzene, toluene or xylene; halogenated aliphatic or aromatic hydrocarbons such as dichloromethane, chloroform or chlorobenzene; esters such as methyl or ethyl acetate; ethers such as diethyl ether or dioxane; ketones such as acetone or methyl ethyl ketone; or formamides such as diethyl-, or dimethylformamide, or any desired mixture of the foregoing can be used.

The reaction temperature can be varied within a wide range. The reaction is generally carried out by heating to the boiling point of the respective solvent or solvent mixture. The reaction can be suitably carried out at from about $-40°$ C. to the boiling point of the solvent. If pyridine is used as halogen halide acceptor, satisfactory reactions can suitably be attained already at the significantly lower temperature range, such as temperatures from about $-40°$ C. to room temperature, due to the known activating effect of pyridine on acyl halides.

Moreover, the compound of formula I when $R^3$ is hydrogen, can be synthesized by cyclizing an N-acylaminobutyric acid derivative of formula III

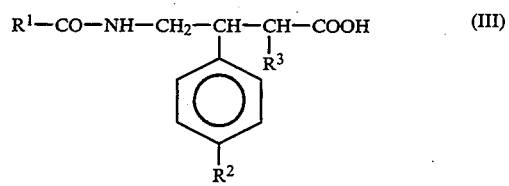

wherein $R^1$ and $R^2$ have the same meanings as given, above, and $R^a$ is hydrogen. The ring-closing reaction can be carried out thermally, suitably at a temperature above the melting point of the compound of formula III. This can be suitably carried out by using water binding materials such as carboxylic acid anhydrides, particularly acetic anhydride; or by the formation of unstable carboxylic acid halides of formula III by halogenating agents, for example, by the reaction of a compound of formula III with thionyl chloride. These unstable carboxylic acid halides of formula III react further with the elimination of hydrogen halide to produce the compound of formula I.

$R^1$, $R^2$, and $R^3$ in the compounds of formula I, can be exchanged in a manner known per se with other substituents of formula I. For example, $R^2$ can be exchanged through selective reactions. Halogen compounds can be synthesized, for example by treating a compound of formula I, when $R^2$ is hydrogen with chlorine or bromine, suitably in the presence of a Lewis acid, such as ferric chloride.

Starting materials of formula II can be prepared, for example by cyclizing an appropriate alkyl 4-amino-3-(4'-$R^2$-phenyl)-butyrate by treatment with sulfuric acid or ethanolic hydrochloric acid, to the corresponding 4-(4'-$R^2$-phenyl)-pyrrolidin-2-ones. For example, 4-amino-3-(4'-$R^2$-phenyl)-butyric acid can easily be thermally cyclized, with dehydration, optionally in the presence of a high-boiling solvent. A compound of formula II in which $R^3$ is $COO_2H_5$ can be most suitably obtained by the reduction of 2-carbethoxy-3-(4'-$R^2$-phenyl)-4-nitrobutyrate esters, suitably by hydrogenation using Raney nickel.

Compounds of formula I have psychotropic effects, which make these compounds suitable for use as cerebroprotective agents. They protect the brain against harmful effects and improve its functional capacity. For example the antiamnesic effect of some compounds in a learning test proved to be 1000 times stronger than that of piracetam and 300 times stronger than that of meclofenoxate or Ca-valproate (see Table 1). The types of investigations that were carried out are those described for memory improving substances, for example, by Sara, S. and David-Remacle, M.: Psychopharmacologia 1974, 36, 59, or Hoffmann, W. and Rostock, A.: Pharmazie 1983, 38, 12, 869. Furthermore, the compounds normalized the learning performance of rats, which had deteriorated due to various injurious factors (chronic alcohol consumption, brain ischemia). It is a further advantage of the compounds that they have no sedating effect. For example, up to a dose of 2,000 mg/kg, no impairment could be observed of coordination ability on the rotating rod.

It proved to be particularly advantageous that the compounds of formula I of the present invention do not have any significant anticonvulsive properties in contrast to other compounds which are known to have nootropic effects, such as carbamazepine, dipropylacetic acid or N-dipropylacetylpyrrolidin-2-one. The experimental findings are of particular importance in that the compounds of formula I do not have any sedating effects, or any, or at most only weakly noted, anticonvulsive properties, because the therapeutic application of the materials for the treatment of mental capacity disorders generally extends over a prolonged period and side effects have to be avoided as much as possible.

The compounds of formula I proved to be very well tolerated. The $LD_{50}$ in animal experiments is more than 2,000 mg/kg of mouse upon intraperitoneal administration.

The effectiveness and toxicity values of compounds of formula I are listed in the table below, and compared against an antiamnestic factor, to those of known compounds having a nootropic effect.

| Test substance No. | Antiamnesically effective dose (mg/kg of rat ip.) | $LD_{50}$ (mg/kg of mouse ip.) |
| --- | --- | --- |
| 1 (from Example 1) | 0.1 | 1,632 |
| 2 (from Example 1) | 100 | >2,000 |
| 3 (from Example 2) | 100 | >2,000 |
| 4 (from Example 3) | 1 | >2,000 |
| 5 (from Example 4) | 1 | >2,000 |
| 6 (from Example 6) | 0.1 | >2,000 |
| Piracetam | 100 | >2,000 |
| Aniracetam | 100 | 1,000 |
| Meclofenoxate | 30 | 856 |
| Ca-Valproate | 30 | 455 |

The invention is further illustrated by reference to the following examples.

EXAMPLE 1

A solution of 32.4 g (0.2 moles) of 4-phenylpyrrolin-2-one in 300 ml of toluene and 35.8 g (0.22 moles) of dipropylacetyl chloride is refluxed for 20 hours, HCl gas escapes during this procedure. After cooling to room temperature, the solution is washed with a saturated potassium carbonate solution and twice with water, dried over $CaCl_2$, the solvent is driven off under vacuum, and the residue is distilled using an oil pump.

N-dipropylacetyl-4-phenyl-pyrrolidin-2-one with the empirical formula $C_{18}H_{25}NO_2$, and (Substance No. 1), $BP_2$: 163° C.–165° C., is obtained as a slightly yellowish, oily liquid.

Yield: 50 g=87% of the theoretical yield.

IR (Film): 1740 (C=O), 1690 (C=O)

In an analogous manner, N-dipropylacetyl-4-(4-chlorophenyl)-pyrrolidin-2-one having the empirical formula $C_{18}H_{24}NO_2Cl$, and (Substance No. 2), $BP_{0.5}$: 200° C.–202° C.) was prepared as a yellowish oil with a 79% yield.

IR (film): 1740 (C=O), 1690 (C=O)

EXAMPLE 2

To a mixture of 16.1 g (0.1 moles) of 4-phenylpyrrolidin-2-one, 19 g (0.11 moles) of 4-methoxybenzoyl chloride and 150 ml of dioxane, 11.1 g (0.,11 moles) of triethylamine are dropwise added. The mixture is then refluxed for 2 hours. After cooling to room temperature, the reaction mixture is poured into water, N-(4-methoxybenzoyl)-4-phenyl-pyrrolidin-2-one (Substance No. 3) crystallizing out. The crude product is filtered off with suction and washed with water. By boiling out the product in 10-fold amount of alcohol and subsequently recrystallizing it from toluene, the product is obtained as colorless crystals of the empirical formula $C_{18}H_{17}NO_2$, melting at 147.5° C.–149° C.

Yield: 19 g—64.3% of the theoretical yield.

IR (KBr): 1750 (C=O), 1660 (C=O)

EXAMPLE 3

4-(4-Chlorophenyl)-pyrrolidin-2-one (19.6 g, 0.1 moles) is dissolved n 150 ml of pyridine and the solution is cooled to 0° C. While stirring, 21 g (0.12 moles) of 4-methoxy-benzoyl chloride are added dropwise. The cooling bath is then removed and stirring is continued for 3 hours at room temperature. The reaction mixture is shaken with 750 ml of 2N HCl, N-(4-methoxybenzoyl)-4-(4-chlorophenyl)-pyrrolidin-2-one of the empirical formula $C_{18}H_{16}NO_3Cl$, (Substance No. 4) crystallizing out. The crystalline precipitate is filtered off, washed with water, dried and recrystallized from the 6-fold amount of toluene.

Melting Point: 163.5°–165° C.

Yield: 19.5g—59% of the theoretical yield.

IR (KBr): 1750 (C=O), 655 (C=O)

EXAMPLE 4

The mixture of 6.8 g (0.032 moles) of 4-chlorophenoxyacetyl chloride, 4.8 g (0.03 moles) of 4-phenyl-pyrrolidin-2-one, 3 ml (0.032 moles) of triethylamine and 30 ml of toluene is stirred for 3 hours at 100°–120° C. and then allowed to cool to room temperature. The precipitate is filtered off, washed first with a small amount of toluene and then with water, and dried in the steam-heated drying oven. N-(4-chlorophenoxyacetyl)-4-phenyl-pyrrolidin-2-one (Substance No. 7) is obtained in a 76.5% yield. After recrystallization from 15-fold the amount of ethanol, the recovered compound of empirical formula $C_{18}H_{16}NO_3Cl$, had a melting point of 129° C.–130° C.

IR (KSr): 1730 (C=O), 1710 (C=O)

N-(4-chlorophenoxyacetyl)-4-(4-chlorophenyl)-pyrrolidin-2-one (Substance No. 5) having the empirical formula $C_{18}H_{15}NO_3Cl_2$, was prepared in a similar manner.

Melting point: 181.5°–183° C. (chlorobenzene)

Yield: 74% of the theoretical yield.

IR (KBr): 1730 (C=O), 1710 (C=O)

N-dipropylacetyl-3-carbethoxy-4-phenyl-pyrrolidin-2-one (substance 10) was synthesized similarly.

Melting point: 50° C.–51° C. (n-hexane).

The yield was: 76% of the theoretical yield of the compound having the empirical formula of $C_{21}H_{29}NO_4$.

IR (KBr): 1746 (C=O), 1725 (C=O), 1679 (C=O)

EXAMPLE 5

A mixture of 2.9 g (0.18 moles) of 4-phenylpyrrolidin-2-one and nicotinoyl acid chloride, synthesized from 2.52 g (0.02 moles) of nicotinic acid and $SOCl_2$, and 3.6 ml (0.04 moles) triethylamine in 15 ml toluene is heated for 9 hours at 100° C. to 110° C. and the precipitate is filtered off, washed with benzene and water and dried. N-nicotinoyl-4-phenyl-pyrrolidin-2-one (Substance No. 8), melting at 146° C.–147° C. (benzene), is obtained in a yield of 3.1 g, which corresponds to 58.5% of the theoretical yield of the compound having the empirical formula $C_{16}H_{14}N_2O_2$.

IR (KBr): 1746 (C=O), 1617 (C=O)

N-(4-chlorobenzoyl)-4-phenyl-pyrrolidin-2-one (Substance No. 9), which melts at 157° C.–158° C. (benzene) was obtained similarly. The yield was 65.4% of the theoretical yield of the compound having the empirical formula $C_{17}H_{14}NO_3Cl$.

IR (KBr): 1746 (C=O), 1617 (C=O)

EXAMPLE 6

3-Carbethoxy-4-phenylpyrrolidin-2-one (58.3 g, 0.25 moles) and 51 g (0.3 moles) of 4-methoxybenzoyl chloride are added to 250 ml of toluene. Upon addition of 33 g (0.3 moles) of triethylamine, a precipitate commences to form. The suspension is heated slowly to reflux and held at this temperature for 2 hours and then cooled. After that, the reaction material is cooled and the crystalline material formed is filtered off with suction, the dried product is repeatedly stirred up with water and subsequently boiled out with alcohol. After recrystallization from the 4-fold amount of toluene, colorless N-(4-methoxybenzoyl)-3-carbethoxy-4-phenyl-pyrrolidin-2-one (Substance No. 6), which melts at 137°–139° C. (toluene), is obtained. By working up the mother liquors, a yield of 73.5% of the theoretical yield is realized of the compound with the empirical formula $C_{21}H_{21}NO_5$.

IR (KBr): 1750 (C=O), 1725 (C=O), 1675 (C=O)

We claim:

1. The compounds:
N-dipropylacetyl-4-phenyl-pyrrolidin-2-one;
N-dipropylacetyl-4-(4-chlorophenyl-pyrrolidin)-2-one;
N-(4-methyoxybenzoyl)-4-phenyl-pyrrolidin-2-one;
N-(4-methyoxybenzoyl)-4-(4-chlorophenyl)-pyrrolidin-2-one;
N-(4-chlorophenyoxyacetyl)-4-phenyl-pyrrolidin-2-one;
N-(4-chlorophenoxyacetyl)-4-(4-chlorophenyl)pyrrolidin-2-one;
N-dipropylacetyl-3-carbethoxy-4-phenyl-pyrrolidin-2-one;
N-(4-chlorobenzoyl)-4-phenyl-pyrrolidin-2-one;
N-(4-methoxybenzoyl)-3-carbethoxy-4-phenyl-pyrrolidin-2-one;
N-nicotinoyl-4-phenyl-pyrrolidin-2-one; and
pharmaceutically acceptable salts thereof.

2. A pharmaceutical preparation having a cerebroprotective activity, which comprises as an active ingredient a therapeutically effective amount of a compound of claim 1, together with a pharmaceutically acceptable carrier.

3. A process for treating cerebral functional disorders which comprises administering to a patient in need thereof a therapeutically effective amount of a pharmaceutically effective amount of one or more compounds of claim 1.

4. A process for treating cerebral functional disorders which comprises administering to a patient in need thereof a therapeutically effective amount of a pharmaceutical preparation containing active ingredient a compound of claim 1.

* * * * *